United States Patent [19]

Tramonte

[11] Plant 4,420

[45] May 22, 1979

[54] ARALIA PLANT NAMED SILVER QUEEN

[75] Inventor: Billy F. Tramonte, Houston, Tex.

[73] Assignee: Pleasure Plants International, Houston, Tex.

[21] Appl. No.: 933,660

[22] Filed: Aug. 14, 1978

[51] Int. Cl.[2] ..... A01H 5/12

[52] U.S. Cl. ..... Plt./88

[58] Field of Search ..... Plt./88

*Primary Examiner*—Robert E. Bagwill

*Attorney, Agent, or Firm*—Rummler and Snow

[57] ABSTRACT

A new and distinct tropical indoor variety of Aralia distinguished by its light green leathery leaves which have a silver white margin completely around the tri-pinnately lobed leaf outline, by its more self-branching and compact growth habit, and by its more abundant densely growing foliage.

1 Drawing Figure

BACKGROUND OF THE NEW PLANT

This new variety of Aralia was found by me as a sport of a Parsley Leaf Aralia plant growing in greenhouse at my nursery at Houston, Tex. Because of its unusual foliage, I reproduced this sport by means of stem cuttings with the object of developing a new line of Aralia plants for indoor culture. Propagation of the plant through successive generations at Houston, Tex., has demonstrated that its distinctive characteristics hold true from generation to generation and appear to be firmly fixed.

DESCRIPTION OF THE DRAWING

My new Aralia plant is illustrated by the accompanying photographic drawing which in the lower view shows a young plant of the new variety, in full color, to illustrate the distinctive nature of the foliage of this variety and its self-branching habit. The upper view shows the original discovery growing on a stem from the base of the parent plant.

DESCRIPTION OF THE NEW PLANT

The following is a description of my new Aralia plant as observed in nursery at Houston, Tex., with color designations according to the R.H.S. Colour Chart published by The Royal Horticultural Society of London, England.

Origin: Sport.

Parentage: Parsley Leaf Aralia (unpatented).

*Botanic name.—Polyscias fruticosa elegans.*

*Common name.*—Variegated Parsley Leaf Aralia.

Form: Bush.

Shape: Pyramidal.

Height: From 18 inches to a maximum of about 3 feet.

Growth: Hardy and upright.

Growth rate: About 10 to 12 inches per year.

Branching character: Self-branching.

Foliage: Abundant — leaf nodes being about ¾ to 1 inch apart.

*Leaf.*—Size — Mature leaf, about 3 inches long and 2 inches wide.

*Leaflets.*—6 to 8 in pinnately compound arrangement. Size: About ½ to 1 inch long and ½ inch wide. Shape: Tri-pinnately cut and lobed, with an acuminate base. Texture: Leathery. Color: Upper side — Green 137A with a continuous marginal band of White 155B. Under side — Green 138B with margin of White 155B. Petiole: About 2 to 3 inches long.

My new tropical indoor Aralia is quite like the parent plant in its growth habit and ultimate size. Its foliage is somewhat more dense, however, providing a very compact pyramidal appearance for the fully grown plant and this plant form, comprising a mass of light green, leathery leaflets, each of which has a silvery white edging, provides a novel distinctiveness for this plant that makes it an attractive and decorative house plant.

I claim:

1. A new and distinct variety of Aralia plant substantially as herein shown and described, particularly characterized by its light green, leathery leaves which have their entire margins edged with silver white, and by its more self-branching and compact growth habit and its abundant and dense foliage production.

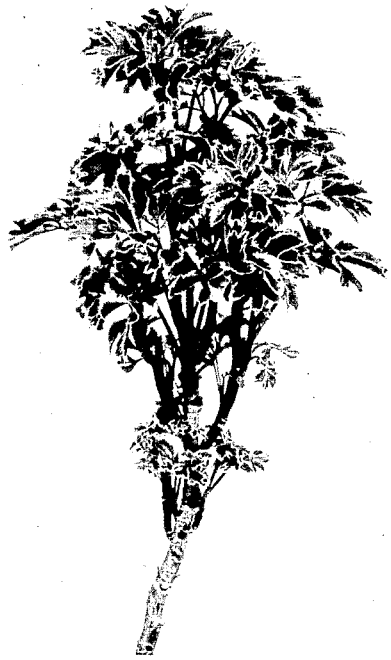
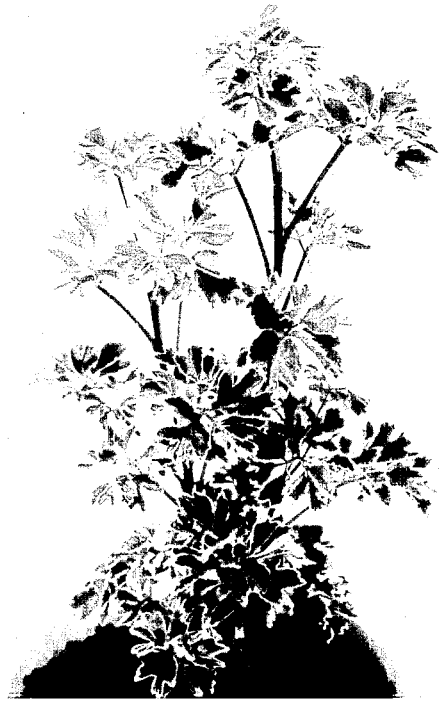

* * * * *